(12) United States Patent
Soltis et al.

(10) Patent No.: US 6,704,605 B2
(45) Date of Patent: Mar. 9, 2004

(54) MEDICAL ELECTRODE ASSEMBLY

(75) Inventors: Brian Soltis, St. Paul, MN (US);
Geordie Alfson, Blaine, MN (US);
Louis M. Buesseler, Bethel, MN (US);
Walt Laroche, Crystal, MN (US);
Jason J. Skubitz, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 108 days.

(21) Appl. No.: 10/062,077

(22) Filed: Jan. 31, 2002

(65) Prior Publication Data
US 2003/0144722 A1 Jul. 31, 2003

(51) Int. Cl.$^7$ .................................................. A61N 1/05
(52) U.S. Cl. ......................................... 607/127; 606/41
(58) Field of Search ........................... 606/41; 607/125, 607/126, 127; 600/372, 373, 374, 375

(56) References Cited

U.S. PATENT DOCUMENTS

| 3,974,834 | A |   | 8/1976  | Kane            |
|-----------|---|---|---------|-----------------|
| 4,106,512 | A |   | 8/1978  | Bisping         |
| 4,570,642 | A |   | 2/1986  | Kane et al.     |
| 5,259,394 | A |   | 11/1993 | Bens            |
| 5,300,108 | A |   | 4/1994  | Rebell et al.   |
| 5,374,286 | A |   | 12/1994 | Morris          |
| 5,447,534 | A |   | 9/1995  | Jammet          |
| 5,649,975 | A |   | 7/1997  | Lindegren et al.|
| 5,716,390 | A |   | 2/1998  | Li              |
| 5,837,006 | A |   | 11/1998 | Ocel et al.     |
| 6,097,986 | A |   | 8/2000  | Janke et al.    |
| 6,463,334 | B1| * | 10/2002 | Flynn et al. ................. 607/127 |

* cited by examiner

Primary Examiner—Roy D. Gibson
Assistant Examiner—Aaron Roane
(74) Attorney, Agent, or Firm—Nikolai & Mersereau, P.A.; C. G. Mersereau

(57) ABSTRACT

A medical lead for tissue stimulation and sensing is provided, the lead having an electrode with an active fixation mechanism. The active fixation mechanism using a conductive spring element or wave washer to maintain electrical contact after extension of the active fixation mechanism. The active fixation mechanism is engaged by rotating a piston within the electrode housing which advances the fixation mechanism distally.

5 Claims, 5 Drawing Sheets

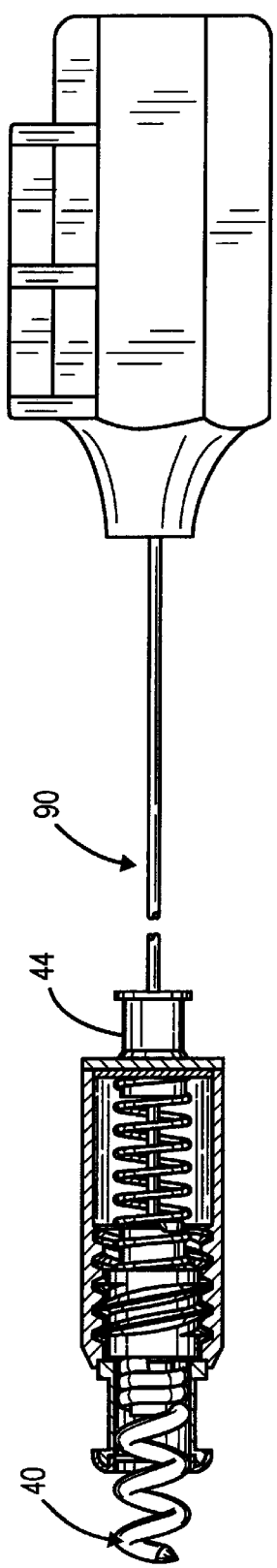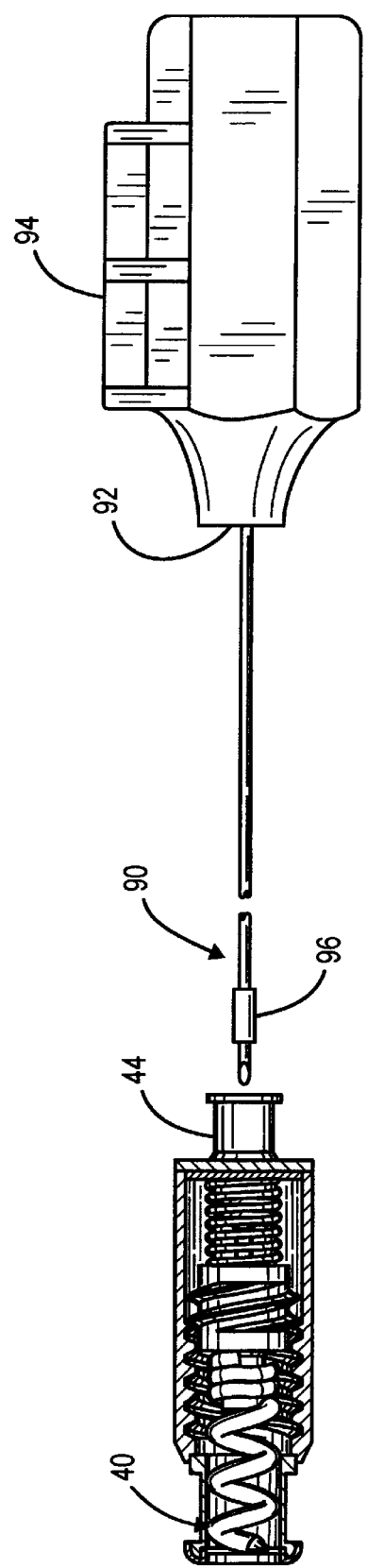
FIG. 5A
FIG. 5B

MEDICAL ELECTRODE ASSEMBLY

BACKGROUND OF THE INVENTION

Field of the Invention

The present invention relates generally to conductive medical leads including fixation electrodes. More particularly, this invention is directed to aspects related to maintaining more reliable electrical conductive contact in implantable fixation lead electrodes and urging such electrodes to remain in an extended, implanted position.

RELATED ART

Implantable leads form an electrical connection between a pulse generator or other electronic device and a tissue or structure in the body. For example, leads transmit electric signals used to stimulate cardiac or nerve tissue in one direction and signals generated by sensors placed in proximity to particular organs or tissues in the opposite direction. Cardiac leads are normally passed through the veins of a patient to form an electrical connection between a pulse generator or other electronic device and the heart.

Medical leads typically include one or more electrodes or sensors at the distal end of the lead. The electrodes are designed to form an electrical connection with a tissue or organ. A flexible conductor electrically connects the electrode to the pulse generator. The electrodes may be passively or actively attached to a target location within the patient. Passive fixation typically employs tines to interlock with the target tissue. Active fixation frequently utilizes a screw helix or similar structure to bore into the tissue to secure the lead. To allow the introduction of the lead to occur benignly without damaging tissue, the screw helix is typically retracted and maintained within a cavity in the electrode housing during insertion. The screw helix may function solely as an anchoring device or may additionally function as an electrode or sensor. When the screw helix functions as an electrode or a sensor, a need exists to maintain the integrity of the electrical connection between the helix and the conductors within the lead body.

Forming a secure electrical junction between the conductors and a screw helix has proven difficult and time consuming. Because of the need to rotate the helix during implantation, a rotatable connection must be formed within the electrode. Related devices have used the contact inherent in a threaded relationship between the piston base of the screw helix and the electrode housing to provide the necessary electrical connection. Thus, the threaded relationship of related art functioned to both advance the screw helix and provide an electrical connection between the screw helix and the conductors. The threaded elements may suffer from transient loss of the electrical contact between the base and the conductors due to the play necessary to allow relative rotation. The beating of the heart may further exacerbate this problem. That is, as the heart beats, the tip electrode is subjected to frequent forces which may result in transient electrical isolation of the screw helix. In application, the transient isolation can provide gaps or spikes in sensed data and interfere with the transmission of pacing stimuli. Therefore, a need exists for a more reliable rotatable connection that provides uninterrupted contact between the electrode and the screw helix.

In addition, the movement of the heart, in time, can cause the extended helix anchor that penetrates the tissue to rotate and retract or withdraw into the electrical assembly. Therefore, a need also exists for an electrode assembly that reliably maintains the helix in an extended orientation after implantation.

The present invention meets the above-described needs and provides additional advantages and improvements that will be evident to those skilled in the art upon further review of the disclosure.

SUMMARY OF THE INVENTION

By means of the present invention, many of the problems associated with prior leads are solved by the provision of an implantable medical lead of superior electrical contact security which, in addition, inhibits unwanted withdrawal of implanted electrode anchors. The present invention provides a secure uninterrupted electrical connection between a screw helix and a conductor.

The medical lead of the invention includes a medical electrode connected to the distal portion of the lead for use to electrically stimulate selected body tissues or to transmit signals from a sensor to a medical device. One illustrative or detailed embodiment of the invention generally involves a hot or conductive helical anchor electrode lead or fixation electrode for a cardiac pacing lead. The device includes an electrode base attached to the distal portion of the elongated lead body. A generally hollow electrode housing which defines an internal cavity is connected to the electrode base through the proximal end of the housing. A distal portion of the internal surface of the electrode housing is provided with helical threads. A piston member having matching external threads is rotatably mounted within the housing cavity and the internal housing threads to thereby move along said housing upon rotation relative thereto. A screw helix electrode-carrying anchor including a sharp distal tine is attached to the piston so as to rotate along with it. The piston and the screw helix electrode and anchor or fixation mechanism are of electrically conducting materials and a resilient conductor member is mounted between the piston and the electrode base to electrically connect the piston with the electrode base so that a positive electrical connection exists between the electrode anchor and the electrode base even when the piston is fully extended.

The electrical housing also may or may not be of a conductive material, depending on the nature of the application. In the case of conductive housings, the resilient conductor member may secure continuous conduction between the piston and the housing.

The resilient conductor member which electrically connects the piston and the electrode base or housing, not only provides a superior uninterrupted electrical contact, but also aids in preventing retraction of the piston once the electrode/anchor is in place in the heart muscle of the patient or other location by urging the piston to remain extended. Whereas other shapes and materials are contemplated, metal compression spring clips and memory-shaped or contact washers have been found useful.

Thus, it can be seen that the present invention provides a secure electrical connection between a screw helix electrode and anchor and a remote conductor in the manner which also aids in maintaining the position of an implanted electrode/anchor of the screw helix class. Other embodiments may occur to those skilled in the art upon familiarization with the contents of the specification.

BRIEF DESCRIPTION OF THE DRAWINGS

FIG. 5A illustrates a stylet as used to rotate a screw helix; and

FIG. 5B illustrates the stylet of FIG. 5A as partially withdrawn with the screw helix retracted.

DETAILED DESCRIPTION

The present invention relates to a variety of implantable medical leads used to electrically stimulate selected body tissues or to transmit signals from a sensor to a medical device. The invention is described generally in the context of a lead body for a cardiac pacing lead for illustrative purposes only. The appended claims are not intended to be limited to any specific end use, example or embodiment described in this specification. It will be understood by those skilled in the art that the lead body of the present invention may be used in a wide variety of implantable leads including, but not limited to, neurostimulation leads, pacing leads, cardiac sensing leads, defibrillation leads, and other leads as will be recognized by those skilled in the art. Further, the numbers are repeated throughout the figures where the individual elements are substantially identical to one another.

Figure 1:
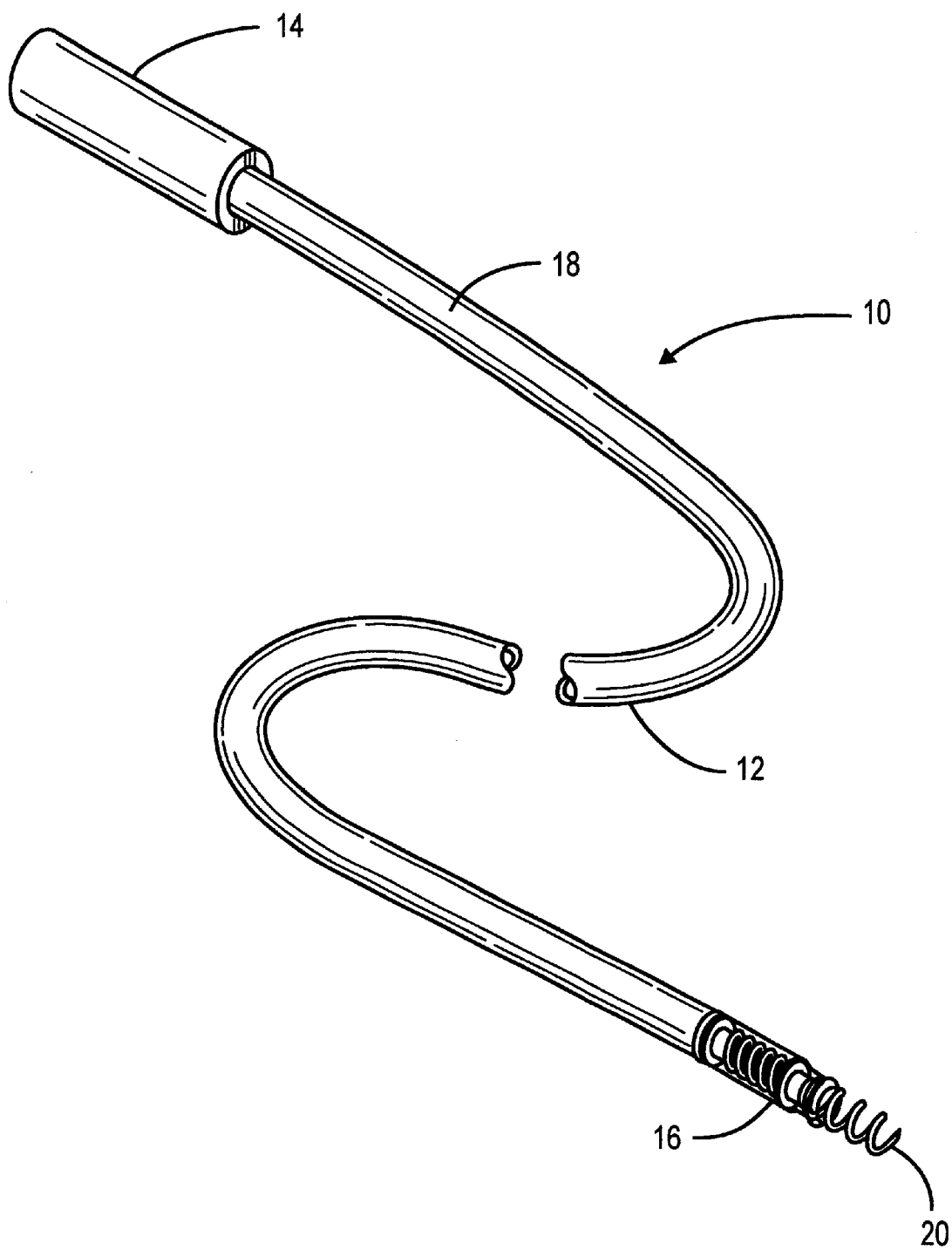
FIG. 1 illustrates schematically a lead employing an electrode in accordance with the present invention.

FIG. 1 schematically illustrates a lead 10 suitable for use in accordance with the present invention. Lead 10 is generally configured to conduct electric current between a medical device and a patient. Lead 10 typically includes a lead body 12, a connector 14 and at least one electrode 16. The lead body 12 also typically includes an internal passage or lumen 18. Lumen 18 is generally configured to allow passage of a stylet during implantation or explantation. The stylet is typically configured to engage a screw helix 20 or other fixation mechanism, as better shown and described in relation to FIGS. 5A and 5B. The stylet is configured to facilitate rotation of the helix to secure the distal end of lead 10 to a target tissue.

Figure 2A:
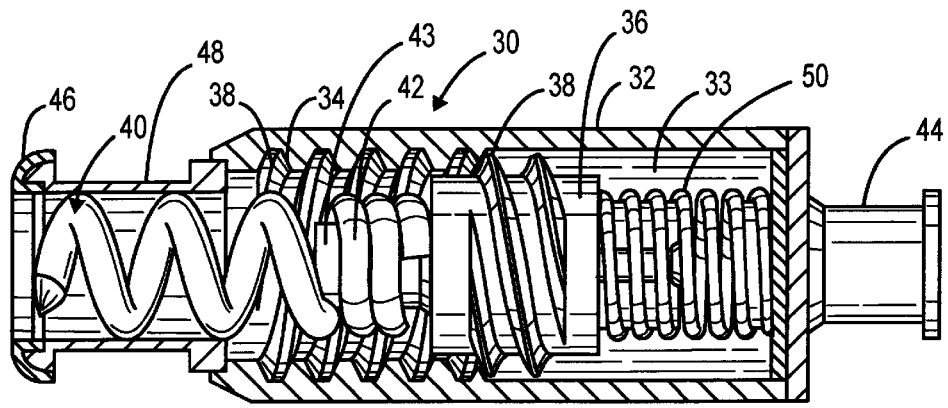
FIG. 2A illustrates a side view partially in section of an electrode assembly in accordance with the invention with the screw helix retracted.
Figure 2B:
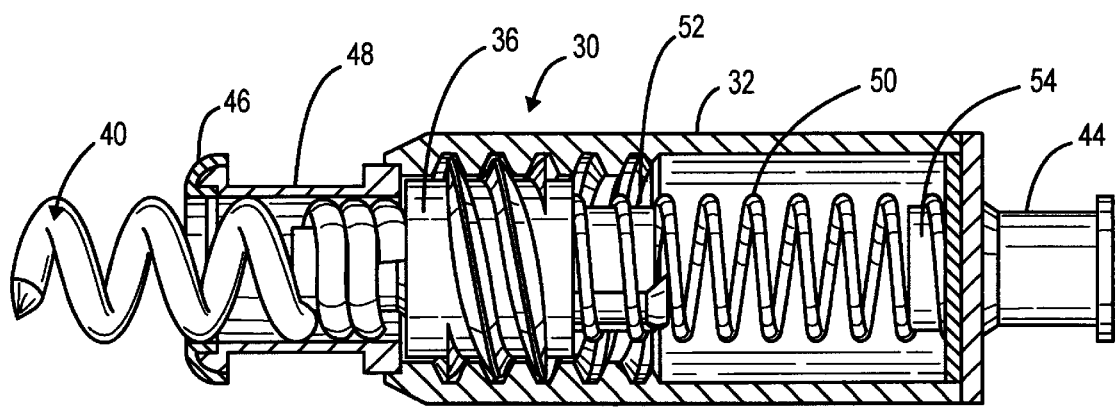
FIG. 2B illustrates a view similar to that of FIG. 2A with the screw helix extended.

FIGS. 2A and 2B illustrate an electrode 30 in accordance with the present invention. Electrode 30 includes an electrode housing 32 which defines a hollow interior chamber 33 and is provided with internal threads illustrated at 34 over a generally distal portion of its length. A piston member 36 is provided which has external threads 38 which match the internal threads 34 of the housing 32. A screw helix, electrode and anchor or fixation device 40 has a proximal end 42 fixed to the distal end 43 of the piston member 36 and a generally hollow electrode base 44 is provided at the proximal end of the housing. In addition, electrode 30 may further include in certain embodiments a terminal electrode device 46 at the distal end of the electrode housing 32. Electrode housing 32 further defines a cavity 48 into which screw helix 40 is withdrawn and resides during implantation and explantation. Electrode housing 32 may be constructed of a conductive or an insulating material in this embodiment. When composed of a conductive material, electrode housing 32 may also function as part of the circuit with the piston and screw helix or may itself act to confer an electrical stimulus to the patient or may function as a conductor to conduct an electrical current to terminal electrode device 46. When the housing composed of an insulating material, screw helix 40 functions alone to confer the electrical stimulus to and receive electrical signals from the patient. In addition, electrode base 44 is provided for electrically connecting electrode 16 to the conductors insulated within lead body 12. Electrode base 44 may be electrically continuous with electrode housing 32 when electrode housing 32 is constructed of a conductive material.

In the embodiment of FIGS. 2A and 2B, a compression spring 50 is mounted between the proximal end 52 of the piston 36 and the distal end 54 of the electrode base 44. The spring 50 is attached to both the piston 36 and the electrode base 44 at 52 and 54, respectively, so that a continuous electrical connection is provided therebetween regardless of the position of the piston in the housing. The spring 50 may be of any conductive material, such as spring steel, suitable for making such springs and one which is compatible with the other conductive parts of the system. The force exerted by the spring 50 even as the electrode including the screw helix 40 is fully extended is sufficient to inhibit retraction of the screw helix 40 for the duration of implantation in moving tissue as, for example, the tissue of a beating heart. FIG. 2B illustrates the electrode in the fully extended position with the screw helix 40 and the compression spring 50 in their nominal fully extended positions as might occur when the device is implanted.

Figure 3A:
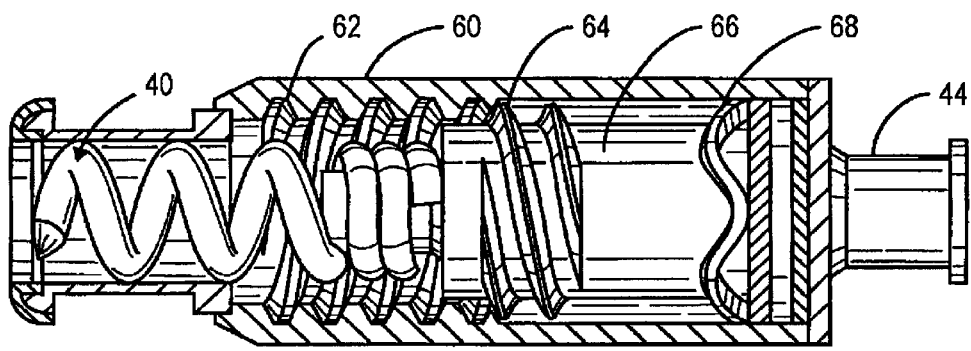
FIG. 3A depicts a side view partially in section of an alternate embodiment of the electrode assembly of FIG. 2A with the screw helix retracted.
Figure 3B:
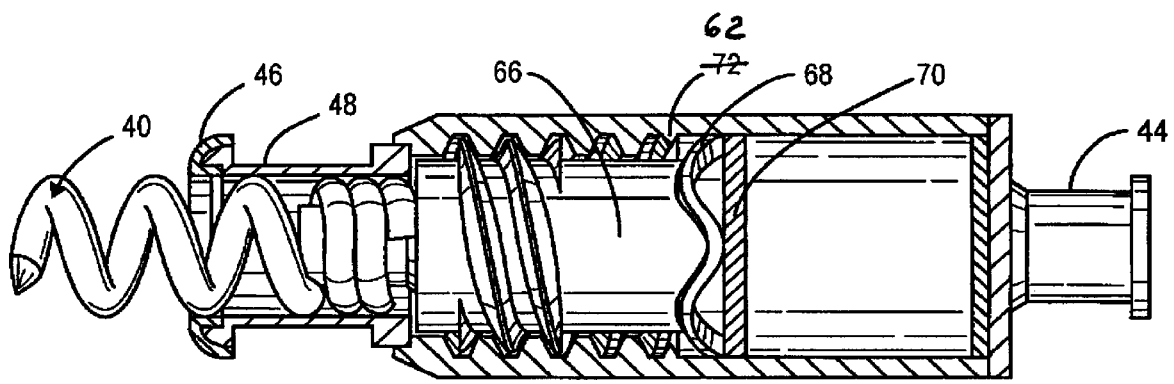
FIG. 3B illustrates a view substantially similar to FIG. 3A with the screw helix extended.
Figure 3C:
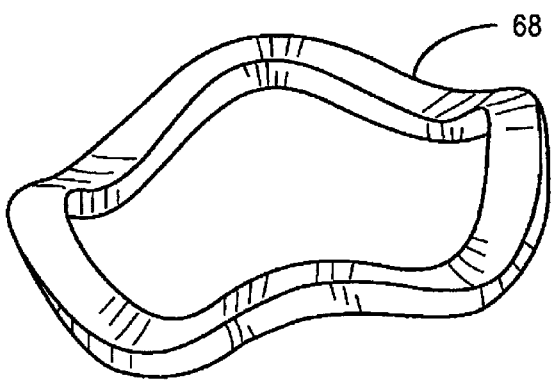
FIG. 3C illustrates a perspective view of a contact washer in accordance with the embodiments shown in FIGS. 3A and 3B.

An alternate embodiment illustrated in FIGS. 3A–3C includes a conductive housing 60 with internal threads 62 adapted to receive external threads 64 of a piston member 66, also of a conductive material. In this embodiment, a contact washer 68 maintains the electrical continuity between the electrode housing 60 (and base 44) and the piston 66. The contact washer 68 may be in the form of a wave washer or other uneven washer such as will be recognized by those skilled in the art. This can be seen in FIG. 3B. The distal end of the piston 66 is flanged as at 70 to retain the washer 68 which, when the piston 66 is fully extended, assures good contact between the proximal end flange 70 of the piston 66 and the housing 60. As indicated, this embodiment requires the housing 60 to be of an electrically conductive material.

Figure 4A:
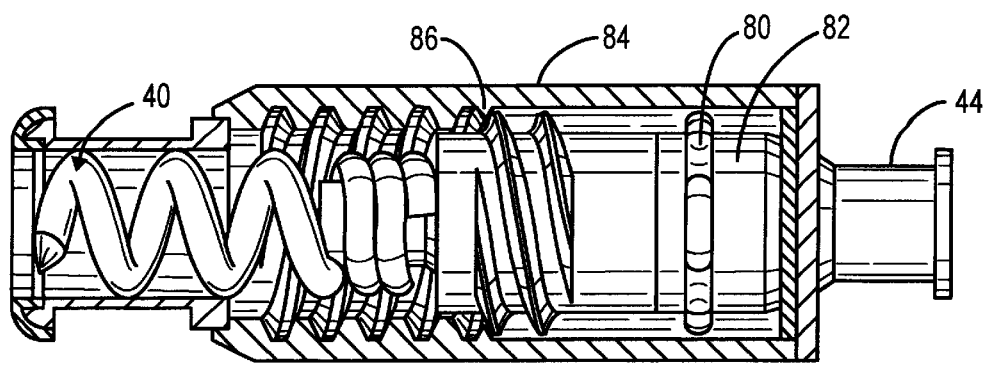
FIG. 4A illustrates a side view partially in section of yet another embodiment of the electrode assembly shown with the screw helix retracted.
Figure 4B:
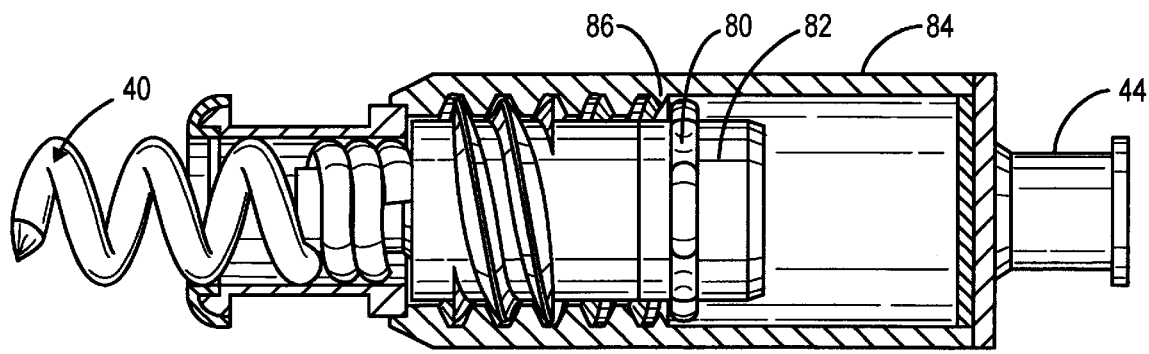
FIG. 4B illustrates a view similar to that in FIG. 4A with the screw helix extended.
Figure 4C:
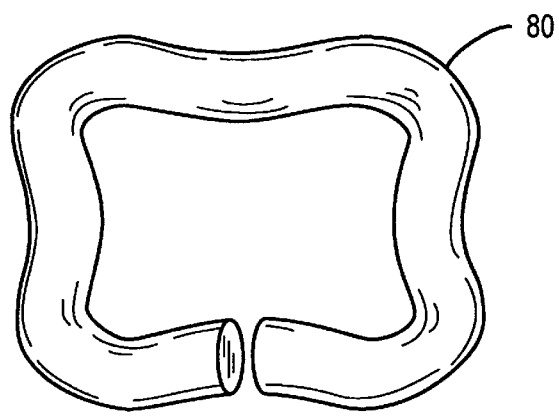
FIG. 4C illustrates a perspective view of a spring clip in accordance with the embodiments shown in FIGS. 4A and 4B.

FIGS. 4A–4C depict yet another embodiment of the implantable electroded lead system of the invention in which a spring clip 80 is utilized with a piston member 82 to assure contact between the side wall of an electrode housing 84 and the piston member 82. Note that the spring clip 80 remains stationery with respect to the piston 82 throughout its travel and remains in continuous contact with the side wall of the electrode housing 84 in the manner of a piston ring. When the piston is fully extended, as shown in FIG. 4B, the spring clip 80 is also in full contact with the raised portion of the housing threads at 86 which aids in maintaining a positive electrical connection. The piston 82 may be provided with a minor circumferential receiving cavity for receiving and maintaining the washer 80 in position, if desired.

FIGS. 5A and 5B further depict a stylet 90 configured to engage and rotate a screw helix 40. The stylet 90 is engaged at its proximal end 92 by a rotating device 94 located beyond the proximal end of hollow lead 10. The stylet 90 further includes a flattened blade area 96 which is used to engage and rotate a helical screw member accessed through the generally hollow electrode base 44.

With respect to any of the described embodiments, in use, a stylet as at 90 is inserted through the lumen 18 of lead 12 until the distal end of the stylet passes through a central opening in the electrode base 44 (not shown) and is received in a conforming cavity within the distal portion of the piston 36, 66, 82 (also not shown) where the blade portion is used to rotate the screw helix in the desired direction by means of rotating device 94. In this manner, the proximal end of the stylet is then rotated. The rotational force is communicated through the length of the stylet to confer a rotational force on the distal end of the stylet. Utilizing the embodiment of FIGS. 2A and 2B as an example, the distal end of the stylet cooperates with the receiving cavity to rotate piston 36 within the cavity 33. The rotation of piston 36 advances screw-helix 40 past the mouth of the cavity 48. Concurrently, spring 50 extends longitudinally maintaining the electrical contact between electrode base 44 and the piston 36. In the case of the embodiment of FIGS. 3A–3C, the contact washer 48 is brought into contact with the piston flange 70 and inner thread ridge 72 or, in the case of the embodiment of FIGS. 4A–4C, the spring clip maintains contact between the side wall of housing 84 and the piston 82 including the raised inner screw flange 86.

All these embodiments form a robust contact which assures electrical continuity between the piston and the electrode base. It will be appreciated that the wave washers as at 68 and 80 also provide and maintain a force that discourages retraction of the respective piston 66, 82 during use.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A medical electrode, comprising:

(a) an electrode base;

(b) a generally hollow electrode housing defining a cavity, the electrode housing being connected to the electrode base at a proximal end of the housing and including internal housing threads and a distal end;

(c) a piston having external threads rotatably mounted within said cavity and said internal housing threads to thereby move along said housing upon relative rotation for extending and retracting;

(d) a screw helix electrode and anchor attached to said piston to rotate therewith;

(e) a resilient conductor for maintaining electrical conductivity between said piston and said electrode base; and (f) wherein said resilient conductor is selected from the group consisting of contact washers, spring clips and compression springs.

2. A medical electrode, comprising:

(a) an electrode base;

(b) a generally hollow electrode housing defining a cavity, the electrode housing being connected to the electrode base at a proximal end of the housing and including internal housing threads and a distal end;

(c) a piston having external threads rotatably mounted within said cavity and said internal housing threads to thereby move along said housing upon relative rotation for extending and retracting;

(d) a screw helix electrode and anchor attached to said piston to rotate therewith;

(e) a resilient conductor for maintaining electrical conductivity between said piston and said electrode base;

(f) wherein said resilient conductor exerts a force when said piston is extended to inhibit retraction of said screw helix electrode; and (g) wherein said resilient conductor is selected from the group consisting of contact washers, spring clips and compression springs.

3. A medical electrode, comprising:

(a) an electrode base;

(b) a generally hollow electrode housing defining a cavity, the electrode housing being connected to the electrode base at a proximal end of the housing and including internal housing threads and a distal end;

(c) a piston having external threads rotatably mounted within said cavity and said internal housing threads to thereby move along said housing upon relative rotation for extending and retracting;

(d) a screw helix electrode and anchor attached to said piston to rotate therewith;

(e) a resilient conductor for maintaining electrical conductivity between said piston and said electrode base;

(f) wherein said resilient conductor exerts a force when said piston is extended to inhibit retraction of said helix; and (g) wherein said resilient conductor is a compression spring connected between said piston and said electrode base.

4. A medical electrode, comprising:

(a) an electrode base;

(b) a generally hollow electrode housing defining a cavity, the electrode housing being connected to the electrode base at a proximal end of the housing and including internal housing threads and a distal end;

(c) a piston having external threads rotatably mounted within said cavity and said internal housing threads to thereby move along said housing upon relative rotation for extending and retracting;

(d) a screw helix electrode and anchor attached to said piston to rotate therewith;

(e) a resilient conductor for maintaining electrical conductivity between said piston and said electrode base; and (f) wherein said electrode housing comprises a conductive material.

5. A medical electrode as in claim 4 wherein said resilient conductor is a contact washer.

* * * * *